United States Patent
Apte et al.

(10) Patent No.: US 11,987,841 B2
(45) Date of Patent: May 21, 2024

(54) SINGLE MOLECULE SEQUENCING AND UNIQUE MOLECULAR IDENTIFIERS TO CHARACTERIZE NUCLEIC ACID SEQUENCES

(71) Applicant: PSOMAGEN, INC., Rockville, MD (US)

(72) Inventors: Zachary Apte, San Francisco, CA (US); Jessica Richman, San Francisco, CA (US); Daniel Almonacid, San Francisco, CA (US); Eduardo Morales, San Francisco, CA (US); Luis Leon, San Francisco, CA (US); Sara W. Bird, San Francisco, CA (US); Juan Ugalde, San Francisco, CA (US)

(73) Assignee: Psomagen, Inc., Rockville, MD (US)

( * ) Notice: Subject to any disclaimer, the term of this patent is extended or adjusted under 35 U.S.C. 154(b) by 269 days.

(21) Appl. No.: 16/649,234

(22) PCT Filed: Oct. 9, 2018

(86) PCT No.: PCT/US2018/055067
§ 371 (c)(1),
(2) Date: Mar. 20, 2020

(87) PCT Pub. No.: WO2019/074960
PCT Pub. Date: Apr. 18, 2019

(65) Prior Publication Data
US 2020/0299763 A1   Sep. 24, 2020

Related U.S. Application Data

(60) Provisional application No. 62/569,853, filed on Oct. 9, 2017.

(51) Int. Cl.
*C12Q 1/6869* (2018.01)
*C12Q 1/6806* (2018.01)

(52) U.S. Cl.
CPC ......... *C12Q 1/6869* (2013.01); *C12Q 1/6806* (2013.01); *C12Q 2525/161* (2013.01);
(Continued)

(58) Field of Classification Search
None
See application file for complete search history.

(56) References Cited

U.S. PATENT DOCUMENTS

2007/0190557 A1    8/2007  Glover, III
2013/0096011 A1*   4/2013  Rava ................... C12Q 1/6869
                                                              702/19

(Continued)

FOREIGN PATENT DOCUMENTS

WO    2014/081456 A1    5/2014
WO    2016/011563 A1    1/2016
WO    2016/172265 A1   10/2016

OTHER PUBLICATIONS

Kivioja et al. Counting absolute Nos. of molecules using unique molecular identifiers. Nature Methods 9(1):72-74. (Year: 2012).*

(Continued)

*Primary Examiner* — Samuel C Woolwine
(74) *Attorney, Agent, or Firm* — Morgan, Lewis & Bockius LLP

(57) ABSTRACT

Embodiments of a method and/or system (e.g., for improved single molecule sequencing, etc.) can include preparing a set of unique molecular identifier (UMI)-based molecules associated with a set of target nucleic acid sequences; facilitating generation of (e.g., generating, etc.) a set of tagged nucleic acid molecules based on the set of UMI-based molecules and a set of nucleic acid molecules corresponding to (e.g., including, etc.) the set of target nucleic acid sequences;

(Continued)

and/or facilitating (e.g., performing, etc.) single molecule sequencing with the set of tagged nucleic acid molecules.

18 Claims, 3 Drawing Sheets

Specification includes a Sequence Listing.

(52) U.S. Cl.
CPC . *C12Q 2535/122* (2013.01); *C12Q 2537/159* (2013.01); *C12Q 2537/165* (2013.01)

(56) References Cited

U.S. PATENT DOCUMENTS

2015/0354000 A1* 12/2015 Borodina ............ C12Q 1/6806 506/2
2016/0319345 A1   11/2016 Gnerre et al.

OTHER PUBLICATIONS

Loose et al. Real-time selective sequencing using nanopore technology. Nature Methods 13(9):751-754. (Year: 2016).*
Mortazavi et al. Mapping and quantifying mammalian transcriptomes by RNA-Seq. Nature Methods 5(7):621-628. (Year: 2008).*
Hong et al. Antibiotic drugs targeting bacterial RNAs. Acta Pharmaceutica Sinica B. 4(4):258-265. (Year: 2014).*
Hoshino & Inagaki. Application of Stochastic Labeling with Random-Sequence Barcodes for Simultaneous Quantification and Sequencing of Environmental 16S rRNA Genes. PLOS ONE 12(1):e0169431. (Year: 2017).*
Ottesen et al. Baseline survey of the anatomical microbial ecology of an important food plant: *Solanum lycopersicum* (tomato). BMC Microbiology 13:114. (Year: 2013).*
International Search Report and Written Opinion dated Jan. 21, 2019 in International Application No. PCT/US18/55067.
Office Action issued in corresponding Japanese Patent Application No. 2020-520597 dated Jun. 14, 2022 with English Translation.
Hoshino, T. and Inagaki, F.: "Application of stochastic labeling with random-sequence bacodes for simultaneous quantificaion and s", PLOS ONE, vol. 1 2 ( 1 ) , JPN7022002827, Jan. 4, 2017 (Jan. 4, 2017), pp. 0169431, SSN: 0004804231.
Kivioja, T. et al.: "Counting absolute Nos. of molecules using unique molecular identifiers", Nature Methods, vol. 9 (1) , JPN7022002828, 2011, pp. 72-74, ISSN: 0004804230.
Loose, M. et al.: "Real-time selective sequencing using nanopore technology", Nat Methods., vol. 1 3 (9) , JPN7022002829, 2016, pp. 751-754, ISSN: 0004804229.
Phipson, B. et al.: "Gene length and detection bias in single cell RNA sequencing protocols", F1000RESEARCH, vol. 6 : 5 9 5, JPN7022002826, Apr. 28, 2017 (Apr. 28, 2017), ISSN: 0004804232.

* cited by examiner

US 11,987,841 B2

SINGLE MOLECULE SEQUENCING AND UNIQUE MOLECULAR IDENTIFIERS TO CHARACTERIZE NUCLEIC ACID SEQUENCES

CROSS-REFERENCE TO RELATED APPLICATIONS

This application is the U.S. National Phase under 35 U.S.C. § 371 of International Application No. PCT/US18/55067 filed on Oct. 9, 2018, which claims the benefit of U.S. Provisional Application No. 62/569,853 filed on Oct. 9, 2017, which are each incorporated in their entirety herein by reference.

TECHNICAL FIELD

The disclosure generally relates to genomics and molecular biology.

BACKGROUND

One key challenge that remains to be addressed when using high throughput sequencing technologies to identify targets in complex mixtures is that overrepresented nucleic acid targets are sequenced several times, impeding the detection of molecules that are underrepresented in the initial nucleic acid pool. Overrepresented template molecules can account for a large portion of the output sequencing reads of a sequencing run due to being sequenced several times, which can waste cycles that could be used to sequence underrepresented template molecules.

Single molecule sequencing (SMS) can include different advantages (e.g., in comparison to sequencing-by-synthesis strategies, etc.). In examples, SMS can allow for the direct characterization of DNA molecules. Examples of current applications of SMS include technologies developed by Pacific Biosciences and Oxford Nanopore. Such platforms can allow for the real time sequencing of DNA molecules, which in association with the appropriate computer hardware and software, can allow for real time processing of the sequencing data.

REFERENCE TO AN ELECTRONIC SEQUENCE LISTING

The contents of the electronic sequence listing (126317-5041_Sequence Listing.txt; Size: 725 bytes; and Date of Creation May 20, 2022), submitted with this application is herein incorporated by reference in its entirety.

DESCRIPTION OF THE EMBODIMENTS

The following description of the embodiments is not intended to limit the embodiments, but rather to enable any person skilled in the art to make and use.

1. Overview.

Figure 1:
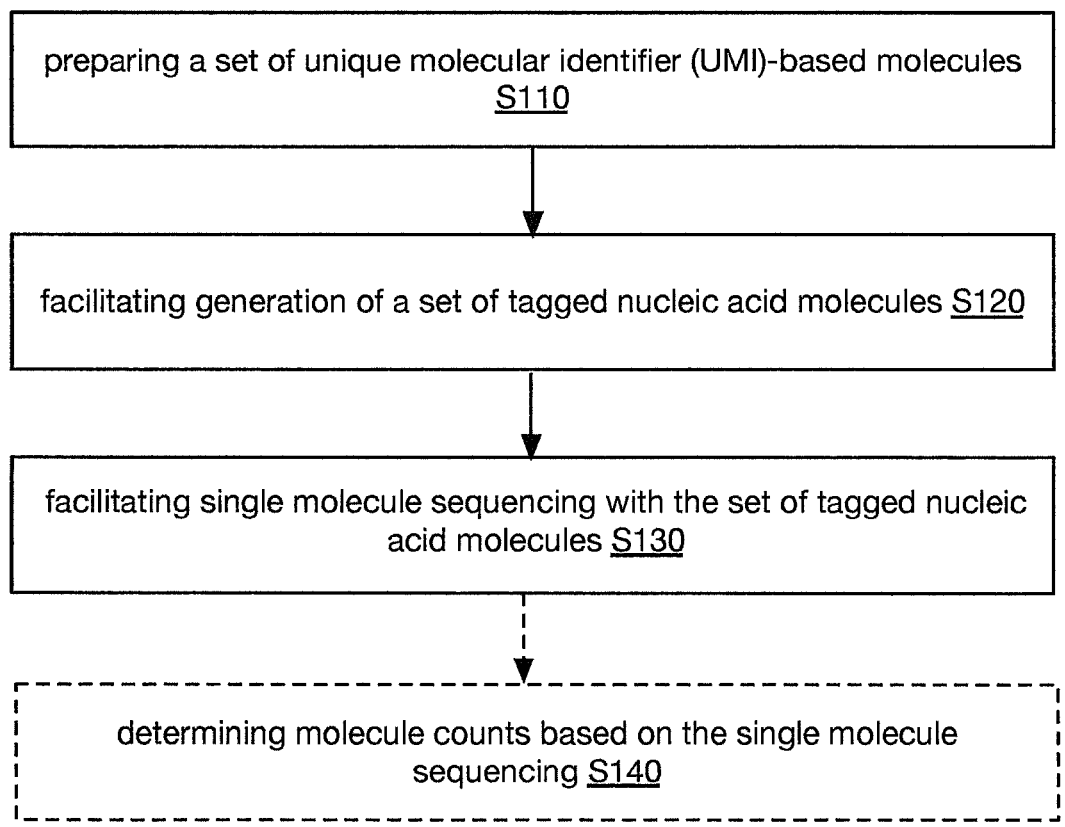
FIG. 1 includes a flowchart representation of variations of an embodiment of a method.
Figure 2:
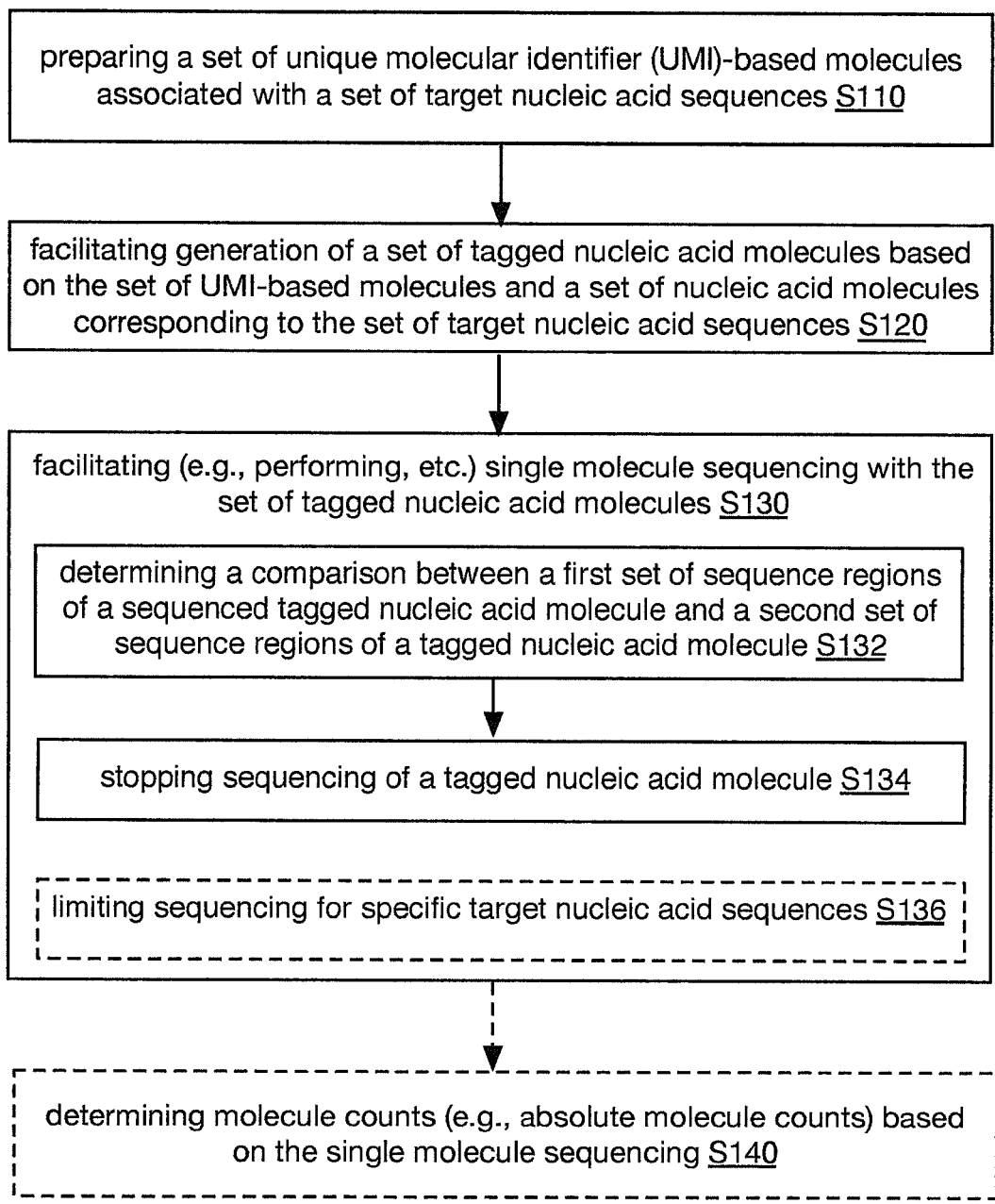
FIG. 2 includes a flowchart representation of variations of an embodiment of a method.
Figure 3:
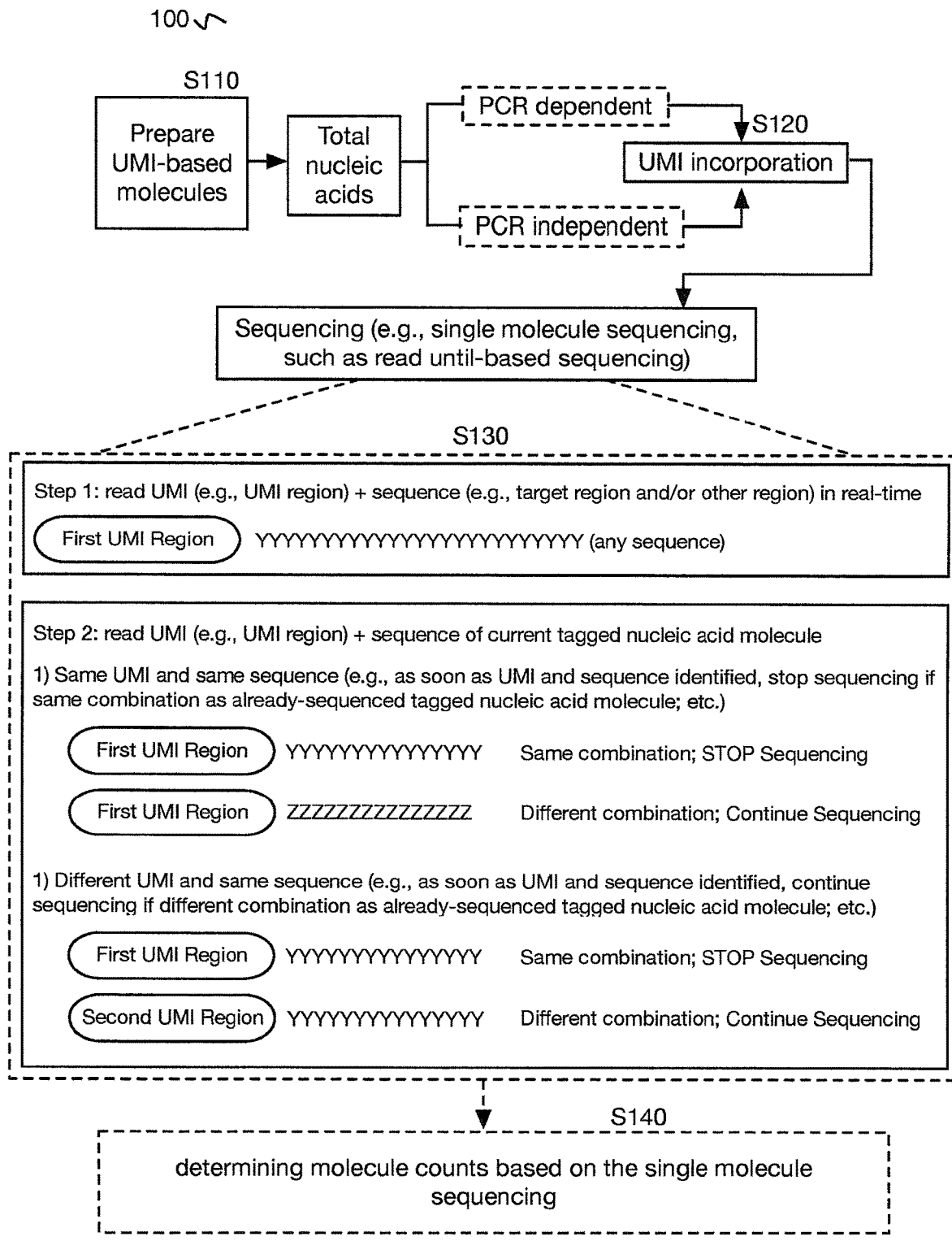
FIG. 3 includes a flowchart representation of variations of an embodiment of a method.

As shown in FIGS. 1-3, embodiments of a method 100 (e.g., for improved single molecule sequencing, etc.) can include preparing a set of unique molecular identifier (UMI)-based molecules associated with a set of target nucleic acid sequences S110; facilitating generation of (e.g., generating, etc.) a set of tagged nucleic acid molecules based on the set of UMI-based molecules and a set of nucleic acid molecules corresponding to (e.g., including, etc.) the set of target nucleic acid sequences S120; and/or facilitating (e.g., performing, etc.) single molecule sequencing with the set of tagged nucleic acid molecules S130. Additionally or alternatively, embodiments of the method 100 can include determining molecule counts based on the single molecule sequencing S140; and/or any other suitable processes.

In a specific example, the method 100 (e.g., for improved single molecule sequencing), can include: preparing a set of UMI-based molecules associated with a set of target nucleic acid sequences (e.g., UMI-based molecules including target-associated regions complementary to target sequence regions of target nucleic acid sequences; etc.); facilitating generation of a set of tagged nucleic acid molecules based on the set of UMI-based molecules and a set of nucleic acid molecules corresponding to (e.g., including, etc.) the set of target nucleic acid sequences, where each tagged nucleic acid molecule of the set of tagged nucleic acid molecules includes: at least one UMI region including a set of random "N" bases, where each random "N" base is selected from any one of an "A" base, a "G" base, a "T" base, and a "C" base, and at least one target region corresponding to a target nucleic acid sequence of the set of target nucleic acid sequences; and/or facilitating single molecule sequencing with the set of tagged nucleic acid molecules, where facilitating the single molecule sequencing includes: determining a comparison between a first set of sequence regions and a second set of sequence regions (e.g., comparing sequence similarity between the first set of sequence regions and the second set of sequence regions; etc.), where the first set of sequence regions includes a first UMI region and a first target region of a sequenced tagged nucleic acid molecule (e.g., sequenced previously in the same sequencing run of the single molecule sequencing; etc.) of the set of tagged nucleic acid molecules, and where the second set of sequence regions includes a second UMI region and a second target region of a tagged nucleic acid molecule of the set of tagged nucleic acid molecules, and stopping sequencing (e.g., during the sequencing run; etc.) of the tagged nucleic acid molecule (e.g., such that the tagged nucleic acid molecule does not contribute to the corresponding molecule count; such that the nucleic acid sequence corresponding to the tagged nucleic acid molecule is not overrepresented; etc.) based on the comparison between the first set of sequence regions and the second set of sequence regions.

In a specific example, the method 100 (e.g., for improved single molecule sequencing) can include: facilitating generation of a set of tagged nucleic acid molecules based on a set of UMI-based molecules and a set of nucleic acid molecules corresponding to a set of target nucleic acid sequences; and/or facilitating single molecule sequencing with the set of tagged nucleic acid molecules, where facilitating the single molecule sequencing includes: determining a comparison between a first UMI region and a second UMI region, where the first UMI region is of a sequenced tagged nucleic acid molecule of the set of tagged nucleic acid molecules, and where the second UMI region is of a tagged nucleic acid molecule of the set of tagged nucleic acid molecules; set of sequence regions and a second set of sequence regions, where the first set of sequence regions includes a first UMI region of a sequenced tagged nucleic acid molecule of the set of tagged nucleic acid molecules, and where the second set of sequence regions includes a second UMI region and a second target region of a tagged nucleic acid molecule of the set of tagged nucleic acid molecules, and stopping sequencing of the tagged nucleic acid molecule based on the comparison between the first UMI region and the second UMI region.

Additionally or alternatively, embodiments of the method 100 and/or a system can include and/or otherwise be associated with processing (e.g., collecting; sample preparation for facilitating portions of embodiments of the method 100; performing portions of embodiments of the method 100 on; etc.) one or more samples (e.g., biological samples) from one or more users (e.g., subjects; humans; animals; patients; plants; etc.), such as biological samples collected from one or more collection sites, which can include one or more of a gut site (e.g., as analyzed based on a stool sample, etc.), skin site, nose site, mouth site, genitals site, and/or other suitable physiological sites; determining microbiome characteristics (e.g., microorganism composition characteristics; microorganism function characteristics; characteristics associated with microorganism-related conditions, such as in relation to diagnosis and/or therapy; etc.) based on microorganism sequence datasets (e.g., microorganism sequence datasets generated based on single molecule sequencing with tagged nucleic acid molecules, such as in relation to portions of embodiments of the method 100; microorganism sequence datasets generated from bioinformatic analysis associated with sequenced UMI regions, such as UMI regions of tagged nucleic acid molecules; microorganism sequence datasets including molecule counts for nucleic acid molecules associated with target nucleic acid sequences; etc.). However, embodiments of the method 100 can additionally or alternatively include any suitable processes.

Embodiments of the method 100 and/or a system can function to improve single molecule sequencing (and/or other sequencing technologies) by use of UMI molecules, such as through improving sequencing outcomes for samples including overrepresented template nucleic acid molecules and underrepresented template nucleic acid molecules; reducing biases associated with amplification processes (e.g., PCR processes) and/or enrichment processes; reducing errors associated with DNA polymerase (e.g., during cluster generation processes; etc.); improving sequencing efficiency (e.g., by reducing wasted sequencing cycles used for overrepresented template nucleic acid molecules; etc.); enabling direct characterization of nucleic acid molecules; and/or any through enabling any other suitable improvements. In a specific example, the method 100 and/or a system can leverage sequencing technologies (e.g., read until-based sequencing technologies, nanopore technologies such as Oxford Nanopore technologies, single molecule sequencing technologies such as Pacific Biosciences single molecule sequencing technologies, etc.) and UMI molecules to perform real-time sequencing and/or processing (e.g., comparing current tagged nucleic acid molecules being sequenced to previously sequenced tagged nucleic acid molecules during the same sequencing run; etc.) while overcoming issues associated with sequencing overrepresented template nucleic acid molecules and underrepresented template nucleic acid molecules.

Additionally or alternatively, embodiments of the method 100 and/or a system can function to quantify microorganisms present in a sample (e.g., based on molecule counts determined from sequencing and/or analysis of UMI regions of tagged nucleic acid molecules; etc.), such as for use in determining microorganism-related characterizations (e.g., in relation to microbiome composition; microbiome function; etc.). However, microorganism quantification can be performed in any suitable manner.

Additionally or alternatively, embodiments of the method 100 and/or a system can function to facilitate microorganism-related detection (e.g., taxonomic detection and/or quantification of organisms of a sample as well as the detection of genes present or expressed in the same sample; detection and/or quantification of organisms with conserved taxonomic genes in a directed fashion, and/or unbiasedly detecting and/or quantifying other eukaryotes, prokaryotes, viral organisms, and/or other suitable microorganisms with characterized or non-previously characterized DNA in one or more biological samples; detection and/or quantification of new, unknown, and/or unidentified potential nucleic acid targets; detection and/or quantification, in an unbiased manner, of known or identified nucleic acid targets such as associated with antibiotic resistance, virulence factors, molecular markers, viral capsid genes, suitable targets of interest; etc.).

Any suitable portions of embodiments of the method 100 and/or a system can include, be for, target, use, process, correspond to, and/or otherwise be associated with one or more of: antibiotic resistance, virulence factors, molecular markers, viral capsid genes, suitable targets of interest. In a specific example, embodiments of the method 100 and/or a system can include sequencing, determining molecule counts (e.g., determining absolute molecules counts based on UMI regions of tagged nucleic acid molecules, for facilitating quantification; etc.), discriminating amongst different target sequences (e.g., by combining use of UMI regions with read until-technology and/or suitable sequencing technology; etc.), selecting specific DNA fragments (e.g., from two or more different libraries, such as 16S with 18S; 16S with HPV (e.g., E1 gene of HPV); and/or other suitable combination of taxonomic or taxonomic-independent sequences; for normalizing abundances of DNA molecules within a sample; etc.), and/or other suitable processes for partial and/or full-length taxonomical marker genes (e.g., 16S rRNA, 18S rRNA, etc.), partial and/or full-length genes and/or markers (e.g., viral capsid genes; genes and/or markers associated with antibiotic resistance; etc.), and/or any suitable genes, markers, and/or targets. In a specific example, the set of target nucleic acid sequences can include at least one of a first set of targets and a second set of targets, where the first set of targets includes a 16S rRNA target and a 18S rRNA target, and where the second set of targets includes a 16S rRNA target and an HPV-associated target. In a specific example, the set of target nucleic acid sequences can include target nucleic acid sequences associated with at least one of antibiotic resistance and a viral capsid gene.

However, embodiments of the method 100 and/or a system can include any suitable functionality.

Portions of embodiments of the method 100 (e.g., facilitating single molecule sequencing S130, etc.) and/or a system preferably include, perform, are associated with (e.g., facilitate library preparation for, etc.), and/or otherwise facilitate single molecule sequencing. Single molecule sequencing can include any one or more of: single molecule real time (SMRT) sequencing (e.g., Pacific Biosciences SMRT sequencing, etc.), nanopore sequencing (e.g., Oxford nanopore sequencing, etc.), long-read sequencing (e.g., Pacific Biosciences long-read sequencing; etc.), Heliscope single molecule sequencing, any generation number of sequencing technologies associated with single molecule sequencing (e.g., second-generation sequencing technologies, third-generation sequencing technologies, fourth-generation sequencing technologies, etc.), and/or any other suitable types of single molecule sequencing.

In a variation, single molecule sequencing can be used in an amplification-independent manner, which can remove biases introduced during PCR-amplification and/or other suitable amplification processes. In a variation, single molecule sequencing can be performed independent of DNA polymerase, thereby avoiding any potential mistakes introduced by DNA polymerase during the steps of cluster generation.

In specific examples, Oxford Nanopore sequencing technology and/or other suitable read until-based technology (e.g., allowing sequencing reads to be read until a condition is met; etc.) can be used, which sequences molecules using nanopores on a membrane, allowing the stopping of the sequencing for a specific pore, and releasing the DNA molecule that is being analyzed. In specific examples, Oxford Nanopore sequencing technology and/or other suitable read until-based technology can at least enable selection of specific DNA fragments (e.g., two different libraries), which can normalize and/or balance the abundance of DNA molecules (e.g., underrepresented DNA molecules; overrepresented DNA molecules; etc.) in a sample; and/or enable limiting the sequencing of specific DNA molecules to certain numbers, such as where instead of generating a large number of reads for a specific DNA molecule, the number of times that a given molecule will be sequenced can be restricted, such as based on UMI regions, target regions, and/or other suitable regions of tagged nucleic acid molecules and/or other suitable molecules.

Additionally or alternatively, embodiments of the method 100 and/or a system preferably include, perform, are associated with (e.g., facilitate library preparation for, etc.), and/or otherwise facilitate any suitable sequencing technology, including any one or more of next generation sequencing (NGS) technologies, capillary sequencing, Sanger sequencing (e.g., microfluidic Sanger sequencing, etc.), pyrosequencing, and/or other suitable sequencing technologies. NGS technologies can include any one or more of high-throughput sequencing (e.g., facilitated through high-throughput sequencing technologies; massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, etc.), any generation number of sequencing technologies (e.g., second-generation sequencing technologies, third-generation sequencing technologies, fourth-generation sequencing technologies, etc.), amplicon-associated sequencing (e.g., targeted amplicon sequencing), metagenome-associated sequencing (e.g., metatranscriptomic sequencing, metagenomic sequencing, etc.), sequencing-by-synthesis, tunnelling currents sequencing, sequencing by hybridization, mass spectrometry sequencing, microscopy-based techniques, and/or any suitable NGS technologies.

Embodiments of the method 100 and/or a system can improve single molecule sequencing and/or other suitable aspects (e.g., described herein) for facilitating (e.g., based on microorganism sequence datasets derived from single molecule sequencing with tagged nucleic acid molecules; etc.) characterizations and/or therapies for one or more microorganism-related conditions, which can include one or more of: diseases, symptoms, causes (e.g., triggers, etc.), disorders, associated risk (e.g., propensity scores, etc.), associated severity, behaviors (e.g., caffeine consumption, habits, diets, etc.), and/or any other suitable aspects associated with microorganism-related conditions. Microorganism-related conditions can include one or more disease-related conditions, which can include any one or more of: gastrointestinal-related conditions (e.g., irritable bowel syndrome, inflammatory bowel disease, ulcerative colitis, celiac disease, Crohn's disease, bloating, hemorrhoidal disease, constipation, reflux, bloody stool, diarrhea, etc.); allergy-related conditions (e.g., allergies and/or intolerance associated with wheat, gluten, dairy, soy, peanut, shellfish, tree nut, egg, etc.); skin-related conditions (e.g., acne, dermatomyositis, eczema, rosacea, dry skin, psoriasis, dandruff, photosensitivity, etc.); locomotor-related conditions (e.g., gout, rheumatoid arthritis, osteoarthritis, reactive arthritis, multiple sclerosis, Parkinson's disease, etc.); cancer-related conditions (e.g., lymphoma; leukemia; blastoma; germ cell tumor; carcinoma; sarcoma; breast cancer; prostate cancer; basal cell cancer; skin cancer; colon cancer; lung cancer; cancer conditions associated with any suitable physiological region; etc.), cardiovascular-related conditions (e.g., coronary heart disease, inflammatory heart disease, valvular heart disease, obesity, stroke, etc.), anemia conditions (e.g., thalassemia; sickle cell; pernicious; fanconi; haemolyitic; aplastic; iron deficiency; etc.), neurological-related conditions (e.g., ADHD, ADD, anxiety, Asperger's syndrome, autism, chronic fatigue syndrome, depression, etc.), autoimmune-related conditions (e.g., Sprue, AIDS, Sjogren's, Lupus, etc.), endocrine-related conditions (e.g., obesity, Graves' disease, Hashimoto's thyroiditis, metabolic disease, Type I diabetes, Type II diabetes, etc.), Lyme disease conditions, communication-related conditions, sleep-related conditions, metabolic-related conditions, weight-related conditions, pain-related conditions, genetic-related conditions, chronic disease, and/or any other suitable type of disease-related conditions. Additionally or alternatively, microorganism-related conditions can include one or more human behavior conditions which can include any one or more of: caffeine consumption, alcohol consumption, other food item consumption, dietary supplement consumption, probiotic-related behaviors (e.g., consumption, avoidance, etc.), other dietary behaviors, habitué behaviors (e.g., smoking; exercise conditions such as low, moderate, and/or extreme exercise conditions; etc.), menopause, other biological processes, social behavior, other behaviors, and/or any other suitable human behavior conditions. Conditions can be associated with any suitable phenotypes (e.g., phenotypes measurable for a human, animal, plant, fungi body, etc.).

Embodiments of the method 100 and/or a system can be implemented for one or more biological samples from a single user, such as in relation to performing portions of embodiments of the method 100 for facilitating preparation of a sequencing library from the one or more biological samples from the single user, and/or facilitating single molecule sequencing with the sequencing library (e.g., a sequencing library including tagged nucleic acid molecules; etc.). Additionally or alternatively, embodiments can be implemented for biological samples from a set of users (e.g., population of subjects including the user, excluding the user, etc.), where the set of users can include subjects similar to and/or dissimilar to any other subjects for any suitable type of characteristics (e.g., in relation to microorganism-related conditions, demographic features behavior, microbiome composition and/or function, etc.); implemented for a subgroup of users (e.g., sharing characteristics, such as characteristics affecting portions of embodiments of the method 100; etc.); implemented for plants, animals, microorganisms (e.g., from environmental microbial communities; etc.), and/or any other suitable entities. Thus, information derived from a set of users (e.g., population of subjects, set of subjects, subgroup of users, etc.) can be used to provide additional insight for subsequent users (e.g., in relation to experimental parameters used in performing portions of embodiments of the method 100; in relation to sequence region criteria used in stopping sequencing for certain tagged nucleic acid molecules; etc.). In a variation, an aggregate set of biological samples can be associated with and processed for a wide variety of users, such as including users of one or more of: different demographics (e.g., genders, ages, marital statuses, ethnicities, nationalities, socioeconomic statuses, sexual orientations, etc.), different microorganism-related conditions (e.g., health and disease states; different genetic dispositions; etc.), different living situations (e.g., living alone, living with pets, living with a significant other, living with children, etc.), different dietary habits (e.g., omnivorous, vegetarian, vegan, sugar consumption, acid consumption, caffeine consumption, etc.), different behavioral tendencies (e.g., levels of physical activity, drug use, alcohol use, etc.), different levels of mobility (e.g., related to distance traveled within a given time period), and/or any other suitable characteristic (e.g., characteristics influencing, correlated with, and/or otherwise associated with microbiome composition and/or function, etc.). In examples, as the number of users increases, the predictive power of processes implemented in portions of embodiments of the method 100 can increase, such as in relation to characterizing a variety of users based upon their microbiomes (e.g., in relation to different collection sites for samples for the users, etc.), such as where microbiome-related characterizations can be determined based on sequencing outputs from single molecule sequencing described herein. However, portions of embodiments of the method 100 and/or a system can be performed and/or configured in any suitable manner for any suitable entity or entities.

Data described herein (e.g., nucleic acid sequences such as target nucleic acid sequences; UMI sequences; molecule design data such as for UMI-based molecules; sequencing data such as sequencing inputs and/or outputs; sequencing data such as sequencing parameters, for example, for stopping sequencing; data associated with UMI-associated tagging; microorganism sequence datasets; microbiome features; user data; supplementary data; data associated with microorganism-related conditions; microorganism-related characterizations; etc.) can be associated with any suitable temporal indicators (e.g., seconds, minutes, hours, days, weeks, etc.) including one or more: temporal indicators indicating when the data was collected (e.g., temporal indicators indicating when a sample was collected; etc.), determined (e.g., temporal indicators indicating when sample processing operations were started, completed; temporal indicators indicating when a tagged target molecule was sequenced, and/or associated data stored; etc.), transmitted, received, and/or otherwise processed; temporal indicators providing context to content described by the data; changes in temporal indicators; and/or any other suitable indicators related to time. Molecules and/or any suitable biological components described herein can include any suitable size (e.g., sequence length, etc.). Comparisons between sequence regions and/or other suitable components can be along any suitable aspect, including any one or more of: sequence similarity (e.g., in percentage; in number of bases; in relation to any suitable sequence region including UMI regions and/or target regions; etc.), complete sequence match, sequence dissimilarity, sequence position, type of target, type of sequence regions, type of associated microorganisms, type of microorganism-related conditions, and/or any other suitable aspects.

Additionally or alternatively, parameters, metrics, inputs, outputs, and/or other suitable data can be associated with value types including any one or more of: scores, individual values, aggregate values, binary values, relative values, classifications, confidence levels, identifiers, values along a spectrum, and/or any other suitable types of values. Any suitable types of data, components (e.g., biological components), products (e.g., of sample processing operations, etc.), described herein can be used as inputs (e.g., for different sample processing operations; models; mixtures; sequencing technologies; etc.), generated as outputs (e.g., of different models; modules; products of sample processing operations; etc.), and/or manipulated in any suitable manner for any suitable components associated with the method 100 and/or a system.

One or more instances and/or portions of embodiments of the method 100 and/or processes described herein can be performed asynchronously (e.g., sequentially), concurrently (e.g., multiplexing; processing a plurality of samples in portions of embodiments of the method 100; parallel data processing associated with sequencing analysis and/or portions of embodiments of the method 100; etc.), in temporal relation (e.g., substantially concurrently with, in response to, serially, prior to, subsequent to, etc.) to a trigger event (e.g., performance of a portion of an embodiment of the method 100), and/or in any other suitable order at any suitable time and frequency by and/or using one or more instances of a system, components, and/or entities described herein.

However, the method 100 and/or a system can be configured in any suitable manner.

2.1 Preparing UMI-Based Molecules.

Embodiments of the method 100 can include preparing (e.g., determining, generating, etc.) a set of UMI-based molecules (e.g., UMI-based primers, etc.) associated with one or more targets (e.g., a set of target nucleic acid sequences; targets associated with microorganisms; etc.) Silo, which can function to prepare molecules used for facilitating tagging (e.g., with UMI-based molecules; UMI regions; linker regions; etc.) of, amplification of, and/or other suitable processing of one or more targets, such as in facilitating generation of a set of tagged nucleic acid molecules.

Targets (e.g., targets of interest; known or identified targets; unknown or previously unidentified targets; etc.) can include any one or more of biomarkers; genes (e.g., gene expression markers, etc.); sequence regions (e.g., genetic sequences; sequences identifying a gene, chromosome, microorganism-related condition, conserved sequences, mutations, polymorphisms; amino acid sequences; nucleotide sequences; etc.); nucleic acids (e.g., genomic DNA, chromosomal DNA, extrachromosomal DNA, mitochondrial DNA, plastid DNA, plasmid DNA, cosmid DNA, phagemid DNA, synthetic DNA, cDNA obtained from RNA, single and double stranded DNA, etc.) cells; small molecules; proteins; peptides; targets associated with one or more microorganism-related conditions (e.g., targets informative of diagnosis, prognosis, prediction, and/or therapy associated with one or more microorganism-related conditions; etc.); targets associated with microorganism composition (e.g., targets indicative of taxonomic classification of microorganisms present in a sample; markers indicating presence, abundance, and/or absence of microorganisms of any suitable taxa; etc.) and/or microorganism function (e.g., targets indicative of functional features associated with microorganisms; etc.); lipids; total nucleic acids; whole microorganisms; metabolites; carbohydrates; and/or any suitable combination (e.g., from multiple libraries, etc.) and/or types of targets. In specific examples, targets can include partial and/or full-length taxonomical marker genes (e.g., 16S rRNA, 18S rRNA, etc.), partial and/or full-length genes and/or markers (e.g., viral capsid genes; genes and/or markers associated with antibiotic resistance; etc.), and/or any suitable genes and/or markers.

UMI-based molecules are preferably associated with (e.g., including a target-associated region including one or more sequence regions complementary to one or more sequence regions of the one or more targets (e.g., nucleic acid targets, etc.); targeting; amplifiable with; processable with; able to tag; etc.) one or more targets (e.g., microorganism-related nucleic acid targets, etc.), but can additionally or alternatively be associated with any suitable components.

In variations, UMI-based molecules can include UMI-based primers (e.g., for use in one or more amplification processes, such as one or more PCR processes; primers including one or more UMI regions; etc.), but can additionally or alternatively include any suitable types of UMI-based molecules for any suitable purpose. In examples, UMI-based primers can omit degenerate primers (e.g., where degenerate primers can introduce biases during PCR processes, such as by favoring amplification of targets more closely matching the sequence of the degenerate primers, thereby resulting in different PCR efficiencies and affecting limit of detection for different templates; where platforms such as minION can enable generation of longer reads, such as where platforms can be used with primers with defined sequences targeting conserved regions; etc.). In a specific example, the set of UMI-based molecules can include UMI-based primers including defined sequence regions targeting a conserved region associated with a plurality of microorganism taxa (e.g., where the use of such primers can reduce biases and/or reduce preferential amplification for target sequences; etc.). In examples, UMI-based primers (e.g., including defined sequence regions targeting conserved regions associated with a plurality of microorganism taxa; etc.) can include a same or similar affinity across different template target, which can reduce negative effects from PCR-based UMI incorporation in generating tagged nucleic acid molecules. In examples, use of UMI-based primers can be used in controlling the amount of sequencing for different targets, such as where sequencing can be allowed to proceed until the amount of data generated allows for identification of different microorganism taxa and/or identification of any suitable targets (e.g., where the amount of sequencing, such as the number of sequenced nucleic acid molecules and/or the sequencing read depth, required to identify a target can vary depending on the specific target; etc.).

UMI-based molecules (and/or other suitable molecules, such as primers and/or other molecules described herein) preferably include one or more UMI regions (e.g., where a UMI-based molecule can include a single UMI region; where a UMI-based molecule can include a plurality of UMI regions; etc.). A UMI region can include a set of random "N" bases (e.g., N deoxynucleotide bases), where each random "N" base is selected from any one of an "A" adenine base, a "G" guanine base, a "T" thymine base, and a "C" cytosine base. "N" bases can be continuous (e.g., a strong of "N" bases, etc.), separated (e.g., by defined bases; by any suitable sequence regions; etc.), and/or be located at any suitable sequence position of the UMI-based molecule. UMI regions can include any suitable sequence length (e.g., at least 2 "N" bases; fewer than 21 "N" bases; any suitable number of "N" bases; etc.). In specific examples, UMI regions (e.g., for a given reaction; for a given tagging process; etc.) can each include a fixed length (e.g., 10 nucleotides in length; etc.). In a specific example, different reactions can be based on UMI regions of different lengths (e.g., all UMI regions including 10 nucleotides in length for a first reaction; all UMI regions including 15 nucleotides in length for a second reaction; other reactions including UMI regions with variable length, such as UMI regions including lengths in the range of 3 to 15 nucleotides for a third reaction; etc.). However, any number and/or type of UMI regions with any suitable lengths (e.g., fixed lengths; variable lengths; etc.) can be used for a one or more reactions. Additionally or alternatively, UMI sequence regions can include fixed (e.g., non-random, etc.) nucleotide sequences alone, a combination of fixed nucleotide sequences with random nucleotide sequences (e.g. "ATCNNNNN" sequence, "NNATCNNNN" sequence, "NNNNATC" sequence, "NNATCNNGTNNN" (SEQ ID NO:1) sequence, where "N" bases can be random "N" bases, etc.), and/or random nucleotide sequences alone.

UMI region sequence length can be determined based on an amount and/or type of targets to be processes (e.g., quantified, differentiated, starting nucleic acid material, etc.), such as where a longer UMI region can facilitate a larger number of random base combinations and a larger set of unique identifiers (e.g., to be used for analyzing a larger number of types of targets to be differentiated; to be used for analyzing samples including a large number of templates, nucleic acid material, and/or gene variants; etc.). In an example, UMI regions of different length and/or sequences can be used and/or incorporated depending on the nature and amount of the starting nucleic acid material (e.g. nucleic acid extracted from microorganisms from gut, mouth, skin, genital, and/or nose samples, etc.). In specific examples, the number of combinations enabled by the length and/or other characteristics of a set of UMI-based molecules (e.g., UMI regions of the set of UMI-based molecules; etc.) is required to be higher than the number of template nucleic acid molecules present in the starting material by at least a single molecule and up to any given number of combinations.

In an example, the UMI region can include a 4N UMI region (e.g., a UMI region including 4 "N" bases, etc.). In a specific example, the UMI region can include an 8N UMI region, such as for an amplification process of a 16S gene, such as with an addition of one or more tagging facilitation molecules such as one or more of $MgCl_2$, dimethyl sulfoxide (DMSO), a thermostable nucleic acid binding protein (e.g., extreme thermostable single-stranded DNA binding protein, etc.), and/or other suitable components. However, UMI regions can be configured in any suitable manner.

UMI-based molecules (and/or other suitable molecules, such as primers and/or other molecules described herein) preferably include one or more target-associated regions. Target-associated regions preferably include sequence regions (e.g., genetic sequences, etc.) but can additionally or alternatively include any suitable types of components (e.g., any suitable components associated with targets, such as bindable to, couplable to, connectable to, influencing, informing, modifying, and/or with any suitable relationship with targets; etc.). Target-associated regions are preferably associated with (e.g., with sequence complementarity to; targeting; amplifiable with; processable with; etc.) one or more targets (e.g., sequence regions of nucleic acid targets; other suitable components of nucleic acid targets; etc.). In an example, a target-associated region can include a DNA sequence annealable with a complementary target DNA sequence (e.g., of a nucleic acid target). In variations, target-associated regions can be associated with a sequence conserved across a plurality of microorganism taxa. In variations, target-associated regions enable polymerases (e.g., DNA polymerases) to copy and amplify nucleic acid targets and/or other suitable components, but target-associated regions can include any suitable functionality. Target-associated regions can include any suitable length (e.g., at least 15 bases in length; any suitable number of bases; etc.). Alternatively, UMI-based molecules can exclude target-associated regions. However, target-associated regions (and/or other suitable molecules) can be configured in any suitable manner UMI-based molecules (and/or other suitable molecules, such as primers and/or other molecules described herein) can include one or more linker regions (e.g., which can function to improve generation of tagged nucleic acid molecules, such as in relation to primer binding to target sequences of nucleic acid molecules; etc.). Linker regions preferably are without full complementarity (e.g., no complementarity, partial complementarity, etc.) to one or more nucleic acid targets (e.g., nucleic acid targets associated with the target-associated region; etc.). Linker regions can include any suitable length (e.g., where the linker region includes a length fewer than 21 bases, such as for each UMI-based primer of a set of UMI-based primers; a length of any suitable number of bases; etc.). Linker regions are preferably positioned between a UMI region and a target-associated region (e.g., separating a UMI sequence region and a target-associated sequence region; etc.), but can be located at any suitable positions (e.g., any suitable sequence positions; etc.), such as where, for each UMI-based molecule (e.g., for each UMI-based primer of a set of UMI-based primers; etc.), the linker region is positioned between the UMI region and the target-associated region of the UMI-based molecule. In specific example, a linker region can include a sequence of a length limiting any potential negative effects of UMI-based molecules in PCR amplification. Alternatively, UMI-based molecules (and/or other suitable molecules) can exclude linker regions. However, linker regions can be configured in any suitable manner.

UMI-based molecules can include any suitable size (e.g., any suitable sequence length, etc.), and any suitable number and/or types of UMI-based molecules can be prepared and/or used in portions of embodiments of the method 100.

In variations, preparing UMI-based molecules can include designing UMI-based molecules based on computational approaches and/or analytical techniques including classical or modified versions of distance metrics (e.g., Hamming and/or Levenshtein, etc.), and allowing for error correction as well as enabling identification of different template molecules. In specific examples, UMI-based molecules are designed to be different across different template molecules. In specific examples, the use of distance metrics allows for controlling the number of nucleotide changes required to convert a UMI region into another UMI region. In a specific example, to convert a first UMI region ("AAA") into second UMI region ("TTT"), at least three changes are needed; where for the specific example, the simplest way to complete the conversion is to substitute all of the A's with T's in the first UMI region. In specific examples, the use of distance metrics allows for controlling the number of different UMIs that could be used to count different molecules, and additionally or alternatively, as an error correction system. Additionally or alternatively, any suitable distance metrics and/or analytical techniques can be used in designing and/or determining a number of UMI-based molecules. In a specific example, preparing the set of UMI-based molecules includes determining (e.g., controlling) a number of different UMI regions for facilitating the generation of the set of tagged nucleic acid molecules, based on the set of target nucleic acid sequences and a defined limit for the sequencing of the tagged nucleic acid molecules (e.g., a predetermined limit associated with a desired amount of sequencing for a target nucleic acid sequence, etc.).

Preparing UMI-based molecules can be performed before and/or after any suitable portions of embodiments of the method 100 (e.g., before or during generation of tagged target molecules; after generation of tagged target molecules for iterative generation of tagged target molecules; etc.), and/or at any suitable time and frequency. Preparing UMI-based molecules can include providing a set of UMI-based molecules to any suitable entity (e.g., a third party entity, for enabling the third party entity to generate a set of tagged target molecules and perform single molecule sequencing with the set of tagged target molecules; etc.)

However, preparing UMI-based molecules Silo can be performed in any suitable manner.

2.2 Facilitating Generation of Tagged Target Molecules.

Embodiments of the method 100 can include facilitating generation of (e.g., generating, etc.) a set of tagged nucleic acid molecules based on the set of UMI-based molecules and a set of nucleic acid molecules corresponding to (e.g., including, etc.) the set of target nucleic acid sequences S120, which can function to obtain tagged target molecules for facilitating downstream sequencing (e.g., single molecule sequencing; etc.) and/or bioinformatics analyses for determining microorganism-related characterizations (e.g., diagnostics and/or treatment determination for one or more microorganism-related conditions; etc.) and/or suitable analyses (e.g., molecule counting).

Nucleic acid molecules (e.g., to be tagged; etc.) are preferably from one or more samples (e.g., samples collected from one or more gut sites, skin sites, genital sites, nose sites, mouth sites, and/or other suitable body sites; biological samples; etc.).

Tagged target molecules (e.g., tagged target nucleic acid molecules) preferably include one or more targets (e.g., components including targets, such as total nucleic acids and/or nucleic acid fragments including target sequence regions, etc.) tagged with (e.g., attached with; connected to; coupled with; etc.) one or more UMI-based molecules (e.g., UMI regions, linker regions, and/or suitable regions of UMI-based molecules; etc.), but can additionally or alternatively include any suitable components associated with one or more targets and tagged with any suitable molecules. Generating the set of tagged target molecules is preferably based on (e.g., use; process with; perform amplification processes with; etc.) a set of UMI-based molecules (e.g., UMI-based primers, etc.) and one or more biological samples (e.g., tagging components of the one or more biological samples with the set of UMI-based molecules and/or components of the set of UMI-based molecules; etc.), but can additionally or alternatively be based on any suitable components.

Facilitating generation of the set of tagged target molecules can be based on (e.g., includes; uses outputs from; etc.) one or more amplification processes. Amplification processes (e.g., associated with generating the set of tagged target molecules; associated with any suitable portions of embodiments of the method 100; etc.) can include one or more PCR processes (e.g., solid-phase PCR, RT-PCR, qPCR, multiplex PCR, touchdown PCR, nanoPCR, nested PCR, hot start PCR, etc.), but can additionally or alternatively include one or more of helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and/or any other suitable amplification processes. In specific examples, multi-step PCR processes can be used in facilitating generation of tagged target molecules (e.g., tagged nucleic acid molecules, etc.), such as in any suitable manner described in and/or analogous to U.S. application Ser. No. 16/013,858 filed 20-Jun.-2018, which is herein incorporated in its entirety by this reference. Additionally or alternatively, any suitable portions of embodiments of the method 100 and/or a system can include, apply, use, and/or be associated with any suitable approach described in and/or analogous to U.S. application Ser. No. 16/013,858 filed 20 Jun. 2018, which is herein incorporated in its entirety by this reference.

However, performing any suitable PCR processes and/or other amplification processes (e.g., in relation to generating the set of tagged target molecules; in relation to any suitable portions of embodiments of the method 100; etc.) can be performed in any suitable manner. Additionally or alternatively, amplification-independent processes can be used to generate tagged nucleic acid molecules. In an example, different subsets of tagged target nucleic acid molecules can be generated (e.g., a set of tagged target nucleic acid molecules including one or more subsets of PCR-generated tagged target nucleic acid molecules and one or more subsets of PCR-independent tagged target nucleic acid molecules; etc.). In a specific example, facilitating the generation of the set of tagged nucleic acid molecules includes: generating a PCR-amplified subset of nucleic acid molecules based on performing a PCR amplification process with a first subset of nucleic acid molecules of the set of nucleic acid molecules; and generating the set of tagged nucleic acid molecules based on the PCR-amplified subset of nucleic acid molecules and a PCR-independent subset of nucleic acid molecules of the set of nucleic acid molecules.

Generating the set of tagged target molecules can additionally or alternatively be based on (e.g., use; process with; perform amplification processes with; etc.) one or more tagging facilitation molecules (e.g., which can be used to improve efficiency and/or versatility related to tagging, such as incorporation of UMI-based molecules to nucleic acid targets; which can be used to improve amplification processes, such as in relation to efficiency; etc.). Tagging facilitation molecules can include any one or more of MgCl$_2$, dimethyl sulfoxide (DMSO), thermostable nucleic acid binding proteins, betaine, formamide, tween, triton, NP-40, Tetramethyl ammonium chloride (TMAC), bovine serum albumin (BSA), organic and/or inorganic enhancer elements, compounds, salts, small molecules, biomolecules and/or any other suitable molecules configured to facilitate tagging.

Facilitating generation of tagged target molecules (and/or tagging any suitable molecules) can be performed at any suitable time and frequency (e.g., prior to generating sequencing-ready tagged target molecules; during or after generating sequencing-ready tagged target molecules, such as in an iterative product generation approach, etc.). Facilitating generation of tagged target molecules can be based on provision of UMI-based molecules to a third party entity and/or suitable entity (e.g., that performs the sample processing required for generating the tagged target molecules; etc.).

In a variation, generating a set of tagged target molecules can include performing one or more fragmentation processes, ligation processes, and/or other suitable processes (e.g., in addition to or alternatively to PCR based processes, etc.) such as to tag the one or more targets such as nucleic acid targets (and/or other suitable components of the one or more biological samples, etc.) with the UMI-based molecules. In an example, generating the set of tagged target molecules can include generating fragments based on at least one of an enzymatic process and mechanical process (e.g., enzymatic and/or mechanical fragmentation, etc.) with one or more biological samples (e.g., to generate fragments including the one or more nucleic acid targets, such as target sequences corresponding to targets of interest; to generate fragments from the one or more biological samples; etc.); and performing a ligation process (e.g., blunt-end ligation with ligase enzyme; etc.) for the UMI-based molecules and the fragments (e.g., ligating the UMI-based molecules to the fragments; etc.), such as prior to amplifying target molecules (e.g., target NDA; for sequencing library construction; etc.). In an example, generating the set of tagged target molecules can include generating nucleic acid fragments from at least one biological sample; and ligating the set of UMI-based molecules to the nucleic acid fragments. In examples, performing the one or more fragmentation processes and/or ligation processes can result in indiscriminately tagging all available molecules (e.g., in the solution), whereas, in examples, generating the set of tagged target molecules with a PCR process (e.g., described herein, etc.) can facilitate specific targeting (e.g., of target DNA sequences) for UMI tagging. Ligation processes used for UMI tagging can use same, similar, or distinct UMI-based molecules (e.g., to tag generated fragments, and/or other molecules; etc.) from types of UMI-based molecules used in PCR processes for generating tagged target molecules performing fragmentation processes. In specific examples, nucleic acid molecules (e.g., corresponding to target nucleic acid sequences; etc.) can be tagged with UMI-based molecules after enzymatic and/or mechanical fragmentation using blunt-end ligation with ligase enzyme before amplifying tagged target nucleic acid molecules (e.g., for sequencing library construction, etc.). In a variation, of PCR-based labeling, enzymes that generate overhang and/or sticky ends within fragmentation methods can additionally or alternatively be used in combination with any suitable ligation processes, including any combination of blunt-end and sticky-end fragmentation and/or proper ligation processes. In a variation, of PCR based labeling, enzymes that insert DNA sequences (e.g., transposons) in nucleic acid molecules can be used to tag with UMI-based molecules, such as in combination with any suitable ligation process (e.g., described herein, etc.).

However, performing one or more fragmentation processes and/or ligation processes, and/or any suitable processes for facilitating generation of tagged target nucleic acid molecules, can be performed in any suitable manner.

Additionally or alternatively, facilitating generation of tagged nucleic acid molecules can include balancing (e.g., normalizing) libraries of different amplicons, such as in a manner described in and/or analogous to U.S. application Ser. No. 16/125,619 filed 7 Sep. 2018, which is incorporated herein in its entirety by this reference. Balancing libraries of different amplicons, and/or performing suitable portions of embodiments of the method 100 can prevent overrepresented molecules impeding the sequencing of less abundant templates, such as where overrepresented template molecules requiring sequencing for a number of cycles before identification can prevent sequencing of underrepresented molecules. In a specific example, facilitating the generation of the set of tagged nucleic acid molecules can include performing at least one amplification process based on the set of UMI-based molecules and the set of nucleic acid molecules for balancing a set of amplicons associated with underrepresented nucleic acid molecules and overrepresented nucleic acid molecules of the set of nucleic acid molecules. In variations, additional PCR processes (e.g., in a 3-step PCR process; etc.) and/or suitable amplification processes can enable balancing of libraries of different amplicons. However, balancing of amplicon libraries and/or other suitable components can be performed in any suitable manner.

In a variation, generating the set of tagged target molecules can include a combination (e.g., serial combination; parallel combination; etc.) of at least one PCR process and at least one ligation process. For example, generating the set of tagged target molecules can include performing a PCR process with a set of primers (e.g., including one or more target-associated regions, linker regions, and/or any other suitable components, etc.), such as to increase PCR efficiency and target amplification; and performing a ligation process with one or more UMI-based molecules (e.g., including one or more UMI regions, adapter regions, and/or other suitable components, etc.), such as for adding the UMI-based molecules to products of the PCR process (e.g., amplified nucleic acid targets; etc.). In an example, generating the set of tagged target molecule can include performing a PCR process based on at least one biological sample and a set of primers including a target-associated region associated with at least one target of the set of targets; and ligating a set of UMI-based molecules to products of the PCR process. However, performing a combination of at least one PCR process and at least one ligation process can be performed in any suitable manner.

Generating the set of tagged target molecules (and/or suitable portions of embodiments of the method 100) can include performing one or more purification processes (e.g., to purify any suitable components; to remove any suitable components; etc.). In an example, generating the set of tagged target molecules can include performing a purification process with products of the first amplification process to remove UMI-based primers of the set of UMI-based primers (and/or to remove other suitable components, etc.) from the products of the first amplification process. In examples, the method 100 can include performing a purification process for products obtained from amplification processes described herein (e.g., a PCR process used to generate a pool of tagged target molecule products, etc.), such as purifying products obtained from a PCR-based amplification process performed with the first set of UMI-based primers. Purification processes can include any one or more of: silica-based DNA binding mini-columns, Solid Phase Reversible Immobilization (SPRI) magnetic beads (e.g., for upscaling and automation, etc.), precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and/or any suitable purification processes. In a specific example, magnetic beads can enable purification of small amounts of products of PCR processes, such as by electrostatic interaction of DNA with the carboxyl coated bead. Additionally or alternatively, purification processes can be performed in any suitable manner (e.g., in relation to any suitable portions of embodiments of the method 100, etc.).

However, generating tagged target molecules (e.g., tagged nucleic acid molecules; etc.) S120 can be performed in any suitable manner.

2.3 Facilitating Single Molecule Sequencing.

Embodiments of the method 100 can include facilitating single molecule sequencing with the set of tagged nucleic acid molecules S130, which can function to leverage single molecules sequencing (e.g., read until-based sequencing, etc.) with UMIs to overcome issues associated with sequencing of overrepresented template molecules in relation to underrepresented template molecules and/or specific target template molecules (e.g., for enrichment; etc.). In specific examples, facilitating single molecule sequencing S130 can function to identify each nucleic acid molecule being sequenced, such as in real-time during a sequencing run. In a specific example, facilitating the single molecule sequencing with the set of tagged nucleic acid molecules includes facilitating the single molecule sequencing for improving detection, reducing sequencing error rate, and/or improving absolute counting of underrepresented nucleic acid molecules from the set of nucleic acid molecules. In a specific example, facilitating the single molecule sequencing with the set of tagged nucleic acid molecules includes facilitating the single molecule sequencing with read until-based technology (and/or suitable sequencing technologies; etc.).

In variations, facilitating single molecule sequencing with the set of tagged nucleic acid molecules S130 can include determining a comparison between a first set of sequence regions of a sequenced tagged nucleic acid molecule and a second set of sequence regions of a tagged nucleic acid molecule S132; stopping sequencing of a tagged nucleic acid molecule S134 (e.g., based on the comparison; by releasing a tagged nucleic acid molecule, such as releasing the tagged nucleic acid molecule from a pore of nanopores on a membrane for Oxford Nanopore sequencing; etc.); limiting sequencing for specific target nucleic acid sequences S136 (e.g., for tagged nucleic acid molecules associated with specific target nucleic acid sequences; etc.); and/or other suitable processes.

Facilitating single molecule sequencing S130 can include performing any suitable portions of facilitating single molecule sequencing S130 (e.g., in relation to S132, S134, S136) in substantially real-time and/or in real-time, such as during a sequencing run. In specific examples, bioinformatic processing of the data generated by the sequencer is done in real-time, to enable comparison of data for sequence tagged nucleic acid molecules to data for current tagged nucleic acid molecules being sequenced, which can enable stopping of sequencing for specific tagged nucleic acid molecules (e.g., stopping of overrepresented nucleic acid molecules, to allow for sequencing of underrepresented nucleic acid molecules; etc.).

Facilitating single molecule sequencing S130 can additionally or alternatively include determining a comparison between sequence regions S132 (e.g., of different tagged nucleic acid molecules, such as of an already-sequenced tagged nucleic acid molecule and a tagged nucleic acid molecule currently being sequenced, etc.), which can function to evaluate one or more conditions for determining whether to stop sequencing for one or more nucleic acid molecules, and/or for any suitable processes.

Comparing sequence regions preferably includes comparing a first UMI region and/or a first target region of a sequenced tagged nucleic acid molecule to a second UMI region and/or a second target region of a tagged nucleic acid molecule (e.g., currently being sequenced, etc.).

IN a specific example, the sequence of the first UMI region can be compared to the sequence of the second UMI region, and the sequence of the first target region can be compared to the sequence of the second target region. In a specific example, determining a comparison can include determining a comparison between a first set of sequence regions and a second set of sequence regions, where the first set of sequence regions includes a first UMI region and a first target region of a sequenced tagged nucleic acid molecule of the set of tagged nucleic acid molecules, and where the second set of sequence regions includes a second UMI region and a second target region of a tagged nucleic acid molecule of the set of tagged nucleic acid molecules; such as where stopping sequencing of the tagged nucleic acid molecule can be based on the comparison between the first set of sequence regions and the second set of sequence regions.

In a specific example, determining the comparison includes determining the comparison between the first UMI region, a first target region of the sequenced tagged nucleic acid molecule, the second UMI region, and a second target region of the tagged nucleic acid molecule, where the first and the second target regions are associated with a target nucleic acid sequence (e.g., the same target nucleic acid sequence, etc.) of the set of target nucleic acid sequences, such as where stopping the sequencing of the tagged nucleic molecule can include stopping the sequencing based on the comparison between the first UMI region, the first target region, the second UMI region, and the second target region (e.g., based on a match between the first UMI region and the second UMI region, and a match between the first target region and the second target region, etc.).

In a specific example, facilitating the single molecule sequencing can include determining the first set of sequence regions (e.g., one or more UMI regions and/or one or more target regions, etc.) of the sequenced tagged nucleic acid molecule; and storing the first set of sequence regions (e.g., at a computing system associated with the sequencing system; at a computing subsystem of the sequencing system; etc.), where determining the comparison between the first set of sequence regions and the second set of sequence regions includes retrieving the first set of sequence regions for the comparison to the second set of sequence regions (e.g., one or more UMI regions and/or one or more target regions of the tagged nucleic acid molecule currently being sequenced; etc.). However, determining one or more comparisons between sequence regions S132 can be performed in any suitable manner.

Facilitating single molecule sequencing S130 can additionally or alternatively include determining stopping sequencing of one or more nucleic acid molecules S134 (e.g., tagged nucleic acid molecules; etc.), which can function to stop sequencing of one or more molecules, such as to enable the sufficient sequencing of underrepresented template molecules, of specific target molecules, and/or of any suitable types of molecules.

As shown in FIG. 3, stopping sequencing of one or more nucleic acid molecules is preferably based on one or more comparisons between sequence regions (e.g., comparisons determined as in S132, etc.). In a specific example, if a given combination of UMI region and target region (and/or suitable non-UMI region) was already sequenced and matches current combination of UMI region and target region being sequenced, a signal (e.g., digital signal, etc.) can be provided to the sequencer and the reaction stopped (e.g., which can thereby enable improvements in the functioning of the sequencing system itself; etc.). In a specific example, stopping sequencing of the tagged nucleic acid molecule can be based on the comparison includes stopping the sequencing of the tagged nucleic acid molecule in response to the first UMI region and the first target region matching the second UMI region and the second target region. In specific examples, read until-based technology can be used for scanning for specific UMI regions, target regions, and/or suitable regions of tagged nucleic acid molecules, and stopping sequencing (e.g., rejecting sequencing reads and/or other suitable outputs) for nucleic acid molecules without specific regions or components (e.g., without UMI regions; etc.). In a specific example, any suitable matches between any suitable regions (e.g., between a first UMI region of a sequenced tagged nucleic acid molecule and a second UMI region of tagged nucleic acid molecule; between other suitable types of regions of nucleic acid molecules; etc.), can be used as conditions for stopping sequencing. In a specific example, stopping sequencing of the tagged nucleic acid molecule can be based on the comparison includes stopping the sequencing of the tagged nucleic acid molecule based on the first UMI region matching the second UMI region.

In specific examples, facilitating the single molecule sequencing can include using processing software to read the data stream (e.g., in real-time, etc.) generated by a sequencing system (e.g., single molecule sequencing system; etc.), which can then be analyzed in determining a comparison between sequencing regions (e.g., as in S132) and/or stopping sequencing of one or more nucleic acid molecules (e.g., as in S134, such as based on the comparison; etc.) and/or continuing reading the nucleic acid molecules. In a specific example, determining the first set of sequence regions (e.g., of a sequenced tagged nucleic acid molecule; etc.), storing the first set of sequence regions, determining the comparison between the first set of sequence regions and the second set of sequence regions (e.g., second set of sequence regions of a tagged nucleic acid molecule, such as a tagged nucleic acid molecule currently being sequenced; etc.), and/or stopping the sequencing of the tagged nucleic acid molecule can be performed in at least substantially real-time during a single sequencing run of the single molecule sequencing.

Additionally or alternatively, stopping sequencing can be based on any suitable condition (e.g., sequencing-related condition), such as based on sequence reads, sequenced regions, defined limits, and/or any suitable conditions. However, stopping sequencing S134 can be performed in any suitable manner.

Facilitating single molecule sequencing can additionally or alternatively include limiting sequencing of nucleic acid molecules, which can function to limit the sequencing of specific nucleic acid molecules (e.g., specific tagged nucleic acid molecules) to certain amounts (e.g., numbers, etc.), such as based on identification of UMI regions, target regions, and/or suitable regions of the specific nucleic acid molecules. Limiting sequencing of nucleic acid molecules can be based on defined limits for target nucleic acid sequences corresponding to the nucleic acid molecules, such as where different defined limits can set limitations on the amount of nucleic acid molecules to be sequenced for a given target nucleic acid sequence. In a specific example, stopping the sequencing of the tagged nucleic acid molecule includes stopping the sequencing based on the comparison and a defined limit for the sequencing of tagged nucleic acid molecules (e.g., where the defined limit has been reached for the target nucleic acid molecule sequence corresponding to the tagged nucleic acid molecule; where the define limit has been reached for the type of tagged nucleic acid molecule; etc.) associated with the first set of sequence regions (e.g., for tagged nucleic acid molecules including sequence regions corresponding to sequences of the first set of sequence regions; etc.), where the set of tagged nucleic acid molecules includes the tagged nucleic acid molecules associated with the first set of sequence regions. However, limiting sequencing of nucleic acid molecules S136 can be performed in any suitable manner.

Facilitating single molecule sequencing S130 can be performed at any suitable time and frequency. Facilitating single molecule sequencing can based on provision of UMI-based molecules and/or facilitating generation of tagged nucleic acid molecules for a third party entity and/or suitable entity (e.g., that performs the sample processing required for generating the tagged target molecules; that performs portions of the single molecule sequencing, such as portions associated with sample loading; where a first party can perform the processes associated with comparison determination, stopping sequencing, and/or limiting sequencing; etc.).

However, facilitating single molecule sequencing S130 can be performed in any suitable manner.

2.4 Determining Molecule Count.

Additionally or alternatively, embodiments of the method 100 can include determining molecule counts based on the single molecule sequencing S140, which can function to determine molecule count-associated metrics for one or more targets (e.g., target nucleic acid sequences; targets associated with tagged nucleic acid molecules; etc.). Molecule counts can include any one or more of absolute molecule counts; counts associated with sequencing read amounts; and/or any suitable molecule count-associated metrics. Determining molecule counts is preferably based on identification and/or analysis of UMI regions of tagged nucleic acid molecules, such as where the UMI sequences of the UMI regions can be used in identification of and/or quantification of one or more targets as present in one or more samples.

In a specific example, the method 100 can include determining absolute molecule counts associated with microorganisms from a sample including the set of nucleic acid molecules, based on the single molecule sequencing of the UMI regions of the set of tagged nucleic acid molecules. In a specific example, the method 100 determining an absolute molecule count associated with the target nucleic acid sequence based on the defined limit for the sequencing of tagged nucleic acid molecules associated with the target nucleic acid sequence, such as where the defined limit (e.g., additionally or alternatively used in stopping sequencing and/or limiting sequencing of nucleic acid molecules; etc.) can be informative and/or used in determining one or more molecule count-associated metrics (e.g., where the defined limit can indicate that the molecule count will not be greater than the count indicated by the defined limit; etc.).

Determining molecule count can be performed at any suitable time and frequency (e.g., in real-time during a sequencing run; in substantially real-time, such as immediately after a sequencing run; at any time after sequencing and/or analysis of UMI regions; etc.).

However, determining molecule counts S140 can be performed in any suitable manner.

3. Other

Embodiments of the method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

Embodiments of the method 100 and/or a system can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of a system and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or a system can be embodied and/or implemented at least in part as a machine configured to receive a computer-readable medium storing computer-readable instructions. The instructions can be executed by computer-executable components that can be integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, a system, and/or variants without departing from the scope defined in the claims.

We claim:

1. A method for improved single molecule sequencing, the method comprising:
    preparing a set of unique molecular identifier (UMI)-based molecules including target-associated regions complementary to target sequence regions of a set of target nucleic acid sequences;
    generating a set of tagged nucleic acid molecules based on the set of UMI-based molecules and a set of nucleic acid molecules corresponding to the set of target nucleic acid sequences by:
        generating a PCR-amplified subset of nucleic acid molecules using a PCR amplification process with a first subset of nucleic acid molecules of the set of nucleic acid molecules; and
        generating the set of tagged nucleic acid molecules using the PCR-amplified subset of nucleic acid molecules and a PCR-independent subset of nucleic acid molecules of the set of nucleic acid molecules, wherein each tagged nucleic acid molecule of the set of tagged nucleic acid molecules comprises:
            a UMI region comprising a set of random "N" bases, wherein each random "N" base is selected from any one of an "A" base, a "G" base, a "T" base, and a "C" base; and
            a target region corresponding to a target nucleic acid sequence of the set of target nucleic acid sequences; and
    performing single molecule sequencing by:
        determining a comparison between a first set of sequence regions and a second set of sequence regions,
            wherein the first set of sequence regions comprises a first UMI region and a first target region of a sequenced tagged nucleic acid molecule of the set of tagged nucleic acid molecules, and
            wherein the second set of sequence regions comprises a second UMI region and a second target region of a tagged nucleic acid molecule of the set of tagged nucleic acid molecules; and
        stopping sequencing of the tagged nucleic acid molecule based on the comparison between the first set of sequence regions and the second set of sequence regions.

2. The method of claim 1, wherein stopping sequencing of the tagged nucleic acid molecule based on the comparison comprises stopping the sequencing of the tagged nucleic acid molecule in response to the first UMI region and the first target region matching the second UMI region and the second target region.

3. The method of claim 2, wherein performing the single molecule sequencing comprises determining the first set of sequence regions of the sequenced tagged nucleic acid molecule; and
    storing the first set of sequence regions, wherein determining the comparison between the first set of sequence regions and the second set of sequence regions comprises retrieving the first set of sequence regions for the comparison to the second set of sequence regions.

4. The method of claim 3, wherein determining the first set of sequence regions, storing the first set of sequence regions, determining the comparison between the first set of sequence regions and the second set of sequence regions, and stopping the sequencing of the tagged nucleic acid molecule are each performed in at least substantially real-time during a single sequencing run of the single molecule sequencing.

5. The method of claim 1, wherein stopping the sequencing of the tagged nucleic acid molecule comprises stopping the sequencing based on the comparison and a defined limit for an amount of nucleic acid molecules to be sequenced for a given nucleic acid sequence.

6. The method of claim 5, wherein preparing the set of UMI-based molecules comprises determining a number of different UMI regions for generating the set of tagged nucleic acid molecules, based on the set of target nucleic acid sequences and the defined limit.

7. The method of claim 1, further comprising determining absolute molecule counts associated with microorganisms from a sample comprising the set of nucleic acid molecules, based on the single molecule sequencing of the UMI regions of the set of tagged nucleic acid molecules.

8. The method of claim 7, wherein performing the single molecule sequencing with the set of tagged nucleic acid molecules comprises performing the single molecule sequencing for improving detection and absolute counting of underrepresented nucleic acid molecules from the set of nucleic acid molecules.

9. The method of claim 1, wherein the set of target nucleic acid sequences comprises at least one of a first set of targets and a second set of targets, wherein the first set of targets comprises a 16S rRNA target and a 18S rRNA target, and wherein the second set of targets comprises a 16S rRNA target and an HPV-associated target.

10. The method of claim 1, wherein stopping sequencing of the tagged nucleic acid molecule comprises limiting sequencing for specific target nucleic acid sequences of the set of target nucleic acid sequences.

11. A method for improved single molecule sequencing, the method comprising:
  generating a set of tagged nucleic acid molecules based on a set of unique molecular identifier (UMI)-based molecules and a set of nucleic acid molecules corresponding to a set of target nucleic acid sequences by:
    generating a PCR-amplified subset of nucleic acid molecules using a PCR amplification process with a first subset of nucleic acid molecules of the set of nucleic acid molecules; and
    generating the set of tagged nucleic acid molecules using the PCR-amplified subset of nucleic acid molecules and a PCR-independent subset of nucleic acid molecules of the set of nucleic acid molecules; and
  performing single molecule sequencing by:
    determining a comparison between a first UMI region and a second UMI region, wherein the first UMI region is of a sequenced tagged nucleic acid molecule of the set of tagged nucleic acid molecules, and wherein the second UMI region is of a tagged nucleic acid molecule of the set of tagged nucleic acid molecules; and
    stopping sequencing of the tagged nucleic acid molecule based on the comparison between the first UMI region and the second UMI region.

12. The method of claim 11, wherein determining the comparison comprises determining the comparison between the first UMI region, a first target region of the sequenced tagged nucleic acid molecule, the second UMI region, and a second target region of the tagged nucleic acid molecule, wherein the first and the second target regions are associated with a target nucleic acid sequence of the set of target nucleic acid sequences, and wherein stopping the sequencing of the tagged nucleic molecule comprises stopping the sequencing based on the comparison between the first UMI region, the first target region, the second UMI region, and the second target region.

13. The method of claim 12, wherein stopping the sequencing of the tagged nucleic acid molecule comprises stopping the sequencing based on the comparison and a defined limit for an amount of nucleic acid molecules to be sequenced for a given nucleic acid.

14. The method of claim 13, further comprising determining an absolute molecule count associated with the target nucleic acid sequence based on the defined limit for the sequencing of tagged nucleic acid molecules associated with the target nucleic acid sequence, for an amount of nucleic acid molecules to be sequenced for a given nucleic acid sequence.

15. The method of claim 11, wherein stopping sequencing of the tagged nucleic acid molecule based on the comparison comprises stopping the sequencing of the tagged nucleic acid molecule based on the first UMI region matching the second UMI region.

16. The method of claim 11, wherein the set of UMI-based molecules comprises UMI-based primers comprising defined sequence regions targeting a conserved region associated with a plurality of microorganism taxa.

17. The method of claim 11, wherein generating the set of tagged nucleic acid molecules comprises performing at least one amplification process based on the set of UMI-based molecules and the set of nucleic acid molecules for balancing a set of amplicons associated with underrepresented nucleic acid molecules and overrepresented nucleic acid molecules of the set of nucleic acid molecules.

18. The method of claim 11, wherein the set of target nucleic acid sequences comprises target nucleic acid sequences associated with at least one of antibiotic resistance and a viral capsid gene.

* * * * *

SEQUENCE LISTING

<160> NUMBER OF SEQ ID NOS: 1

<210> SEQ ID NO 1
<211> LENGTH: 12

```
<212> TYPE: DNA
<213> ORGANISM: Artificial Sequence
<220> FEATURE:
<223> OTHER INFORMATION: Example of UMI region
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 1
nnatcnngtn nn                                                              12
```